(12) United States Patent
Brown

(10) Patent No.: US 10,786,392 B2
(45) Date of Patent: Sep. 29, 2020

(54) EYE MARKER TIP

(71) Applicant: Mindskid Labs, LLC, Wilmington, NC (US)

(72) Inventor: Alan Wesley Brown, Wrightsville Beach, NC (US)

(73) Assignee: Mindskid Labs, LLC, Wilmington, NC (US)

(*) Notice: Subject to any disclaimer, the term of this patent is extended or adjusted under 35 U.S.C. 154(b) by 149 days.

(21) Appl. No.: 15/654,256

(22) Filed: Jul. 19, 2017

(65) Prior Publication Data
US 2017/0312134 A1 Nov. 2, 2017

Related U.S. Application Data

(63) Continuation of application No. 14/597,854, filed on Jan. 15, 2015, now abandoned.

(51) Int. Cl.
*A61F 9/013* (2006.01)

(52) U.S. Cl.
CPC .................................. *A61F 9/0136* (2013.01)

(58) Field of Classification Search
CPC ............ A61F 9/0136; A61F 2090/3933; A61F 2090/3937; A61F 2090/395; A61F 2090/3904; A61F 9/00736; A61F 9/013; A61B 2090/0814; A61B 1/00188; A61B 90/30
See application file for complete search history.

(56) References Cited

U.S. PATENT DOCUMENTS

| 6,113,606 A * | 9/2000 | Dykes ..................... A61F 9/013 606/107 |
| 2006/0025814 A1* | 2/2006 | Hatori .................... A61B 90/00 606/205 |
| 2011/0251630 A1* | 10/2011 | Richardson ........... A61F 9/0136 606/166 |
| 2012/0283523 A1* | 11/2012 | Yadlowsky ......... A61F 9/00763 600/249 |
| 2013/0267783 A1* | 10/2013 | Davis ................. A61B 1/00188 600/200 |

* cited by examiner

*Primary Examiner* — Diane D Yabut
*Assistant Examiner* — Majid Jamialahmadi
(74) *Attorney, Agent, or Firm* — Douglas Tsao; F. Michael Sajovec; Williams Mullen

(57) ABSTRACT

The present invention provides an eye marker tip that includes a base, one or more marking wings, and a marking element attached to a marking wing and configured to deliver ink (or another indicator) to a surface of an eye. Embodiments may include a hollow or translucent post and light channel, or a base having a fixation button, to form a central light shape visible to a patient. Embodiments may include either or both of a magnifying lens and a parabolic light deflector, to form circles of light that may be used in connection with a central light shape to properly align the eye marker tip with a patient's eye.

5 Claims, 10 Drawing Sheets

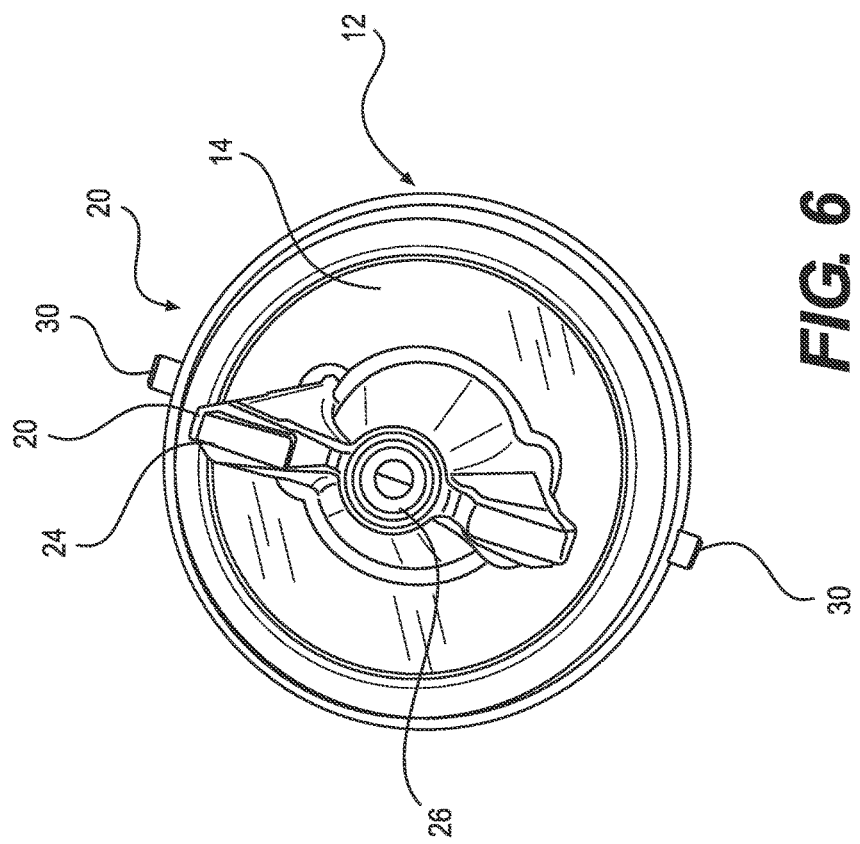

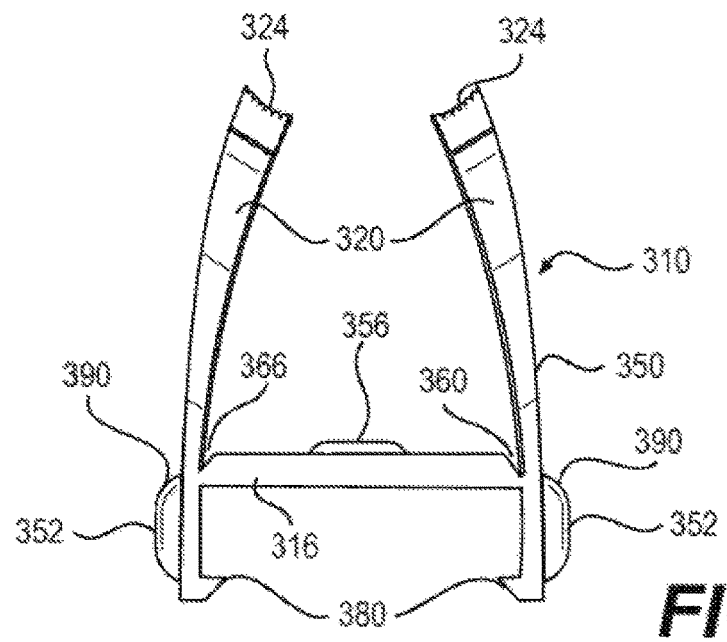
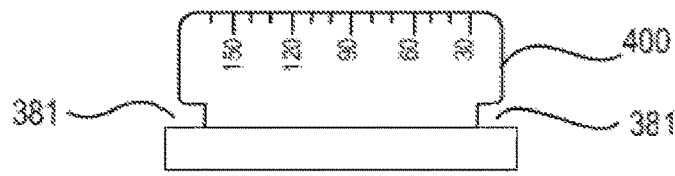
FIG. 9A
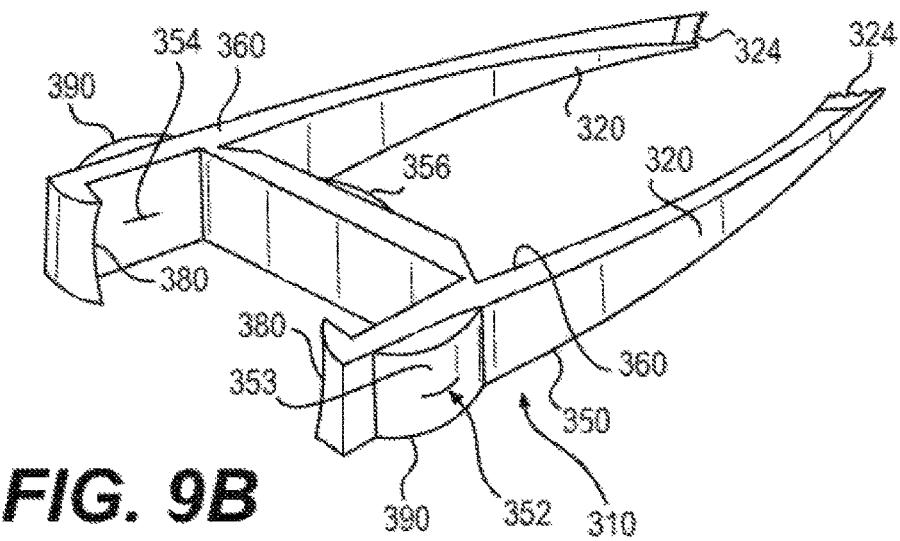
FIG. 9B

EYE MARKER TIP

CROSS-REFERENCE TO RELATED APPLICATIONS

This application is a continuation of U.S. patent application Ser. No. 14/597,854, filed Jan. 15, 2015, the content of which is incorporated in its entirety.

FIELD

The application describes improved eye marker tips for marking the eye.

BACKGROUND

This application addresses the problem of long lasting accurate marks applied to the ocular surface as needed. In the field of refractive surgery there exists a need to place ink marks on the eye in order to orient the treatment of astigmatism. In the field of cataract surgery, a corneal astigmatism can be balanced by an intraocular toric lens implant that has a curved surface that counterbalances the corneal astigmatism. In such methods for treating astigmatism, the eye should be marked before surgery in order to properly position the treatment of the astigmatism.

Patients undergoing such treatments are required to have the operative site marked with a surgical marker before being brought into the operating room. However, conventional marking devices suffer from issues of inadequate ink transfer to the eye surface, principally due to the fact that only a thin layer of ink is being transferred to an ocular surface, and that surface is wet from the ocular tear film. As a consequence, the patient blinks off ink marks from conventional marking devices in a matter of minutes.

Additionally, it is well known that the eye position rotates or undergoes cyclotorsion when the patient moves from a vertical or sitting position to a lying or horizontal position. The change in position creates an error in marking an eye, and the error can be upwards of 20 degrees, which is clinically significant. As a consequence, the best practice is to mark the patient's eye while the patient is in a vertical or sitting position, because that position is the normal position for use of the eyes. However, the best practice often conflicts with the typical operating room sequence of having the patient lying down, prepared for surgery, draped, and ready for the surgeon before the surgeon enters the room. The need to mark the patient in the sitting position delays the normal preparation sequence for surgery. An alternative sequence is to pre-mark a patient in a separate preparation area, in which oral sedation and IVs are administered. The pre-marking may be administered with a surgical ink marker pen to the area where the cornea meets the sclera. Such conventional markers leave a lasting dot of ink not found on the thin film of ink applied with sterile metal markers. However, the placement of surgical ink marker dots is imprecise and over time the dots tend to smear leaving the pin point intended location in question.

The conventional sequence now requires surgeons to mark the patient's brow over the eye having surgery prior to being moved to the operating room. Because every patient gets a correct surgical site identification mark with a surgical marker over the brow, it is convenient for the surgeon to add marks on the eye at the same time. Because conventional metal markers retain only a thin film of ink that is blinked off within minutes, they are not effective for marking outside of the operating room. Consequently, the only lasting marks that can be made before surgery under conventional methods are ink dots placed in the general horizontal and vertical meridians. As noted, these hand placed dots are not precise and tend to smear over time.

BRIEF SUMMARY

As can be seen, the conventional system for marking the eye for treatment of astigmatism is complex, and suffers from limitations with respect to at least the accuracy of the marks placed, how the procedure is performed, and how the patient is prepared for surgery. U.S. patent application Ser. No. 13/427,253, which is fully incorporated by reference, describes improved eye marker devices overcoming the shortfalls of the conventional devices and system for marking the eye for treatment of astigmatism. This application describes improved eye marker tips for use with eye marker devices, such as the devices described in U.S. patent application Ser. No. 13/427,253. The embodiments of eye marker tips described herein are described in the context of the eye marker devices described in U.S. patent application Ser. No. 13/427,253, but the eye marker tips described herein are not meant to be limited to use with the eye marker devices described in U.S. patent application Ser. No. 13/427,253.

The eye marker tips described herein may be utilized on an eye marker device, such as, for example only, the eye marker devices described in U.S. patent application Ser. No. 13/427,253. Embodiments of the eye marker tips described herein may be used in connection with other eye marker devices.

According to some embodiments, an eye marker tip comprises a base, at least one marking wing, and a marking element engaged to the marking wing and configured to deliver ink (or another indicator) to the surface of a patient's eye.

According to some embodiments, the eye marker tip comprises a hollow post. The post may be configured for attachment to a corresponding eye marker device. The post may be configured to allow light to pass from a light source, such as a light source from a corresponding eye marker device, and to the base.

According to yet another embodiment of the present invention, the eye marker tip comprises two marking wings. The marking wings may be on substantially opposite sides of a base, such that marking elements may apply ink markings at a 180-degree angle.

According to some embodiments, the eye marker tip comprises a light channel for allowing light to proceed through the eye marker tip, from a light source, such as a light source from a corresponding eye marker device, and through the base, and ultimately to a patient's eye.

According to some embodiments, the eye marker tip comprises attachment elements for positioning the eye marker tip on a corresponding eye marker device.

According to some embodiments, the eye marker tip is disposable. Some embodiments of the eye marker tip may be entirely disposable. Other embodiments may have a disposable upper portion that may be removed from a lower portion.

According to some embodiments, the eye marker tip is composed entirely or partially of plastic. In some embodiments, portions of components of the eye marker tip are formed from one or more plastics. In some embodiments, a plastic may be clear, transparent, and/or translucent. The plastic may allow light to pass through all or a portion of the eye marker tip to illuminate a surface, such as the surface of a patient's eye.

According to some embodiments, the eye marker tip includes a base having a fixation button. In some embodiments, the fixation button may be disposed on the magnifier lens.

According to some embodiments, the eye marker tip includes a base having a magnifying lens, such that light from a light source may be magnified to form a magnified light shape, such as a circle, when viewed by a patient. A magnifying lens may include an indicator line.

According to some embodiments, the eye marker tip includes a base having a parabolic light deflector or prism. In some embodiments, the parabolic light deflector may be disposed on the magnifier lens. The parabolic light deflector may axially deflect all or a portion of light received from a light source, to form a deflected shape, such as a circle, when viewed by a patient.

According to some embodiments, proper alignment of the eye marker tip relative to a patient's eye may be achieved by aligning light from a central light, such as a hollow or translucent post and light channel or a fixation button, light from a magnifying lens, and/or light from a parabolic light deflector.

According to some embodiments, the eye marker tip includes at least one axis dial disposed on an outer portion of the housing.

According to some embodiments, an eye marker tip may include a stress-breaker feature.

BRIEF DESCRIPTION OF THE DRAWINGS

The eye marker tips illustrated and described herein are made with reference to the various drawings, in which like reference numbers denote like method steps and/or system components, respectively, and in which:

FIG. 6 is a top perspective view of an embodiment of an eye marker tip;

FIGS. 9A and 9B shows a side view and a perspective view, respectively, of another embodiment of an eye marker tip.

DETAILED DESCRIPTION

Figure 1:
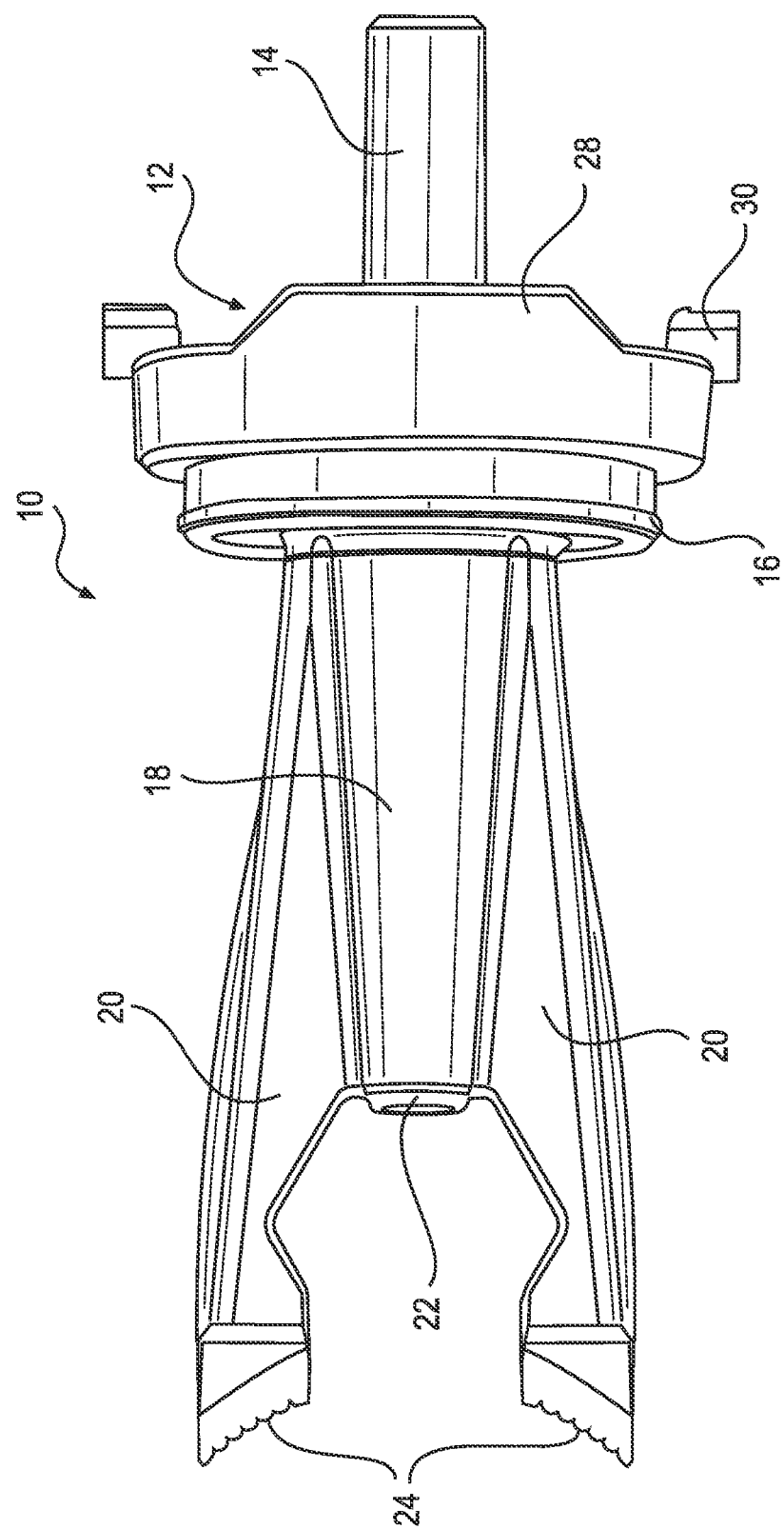
FIG. 1 is a perspective view of an embodiment of an eye marker tip.

Referring now to the drawings, an embodiment of an eye marker tip 10 is illustrated in FIGS. 1-6. Eye marker tip 10 may be configured for use with an eye marker device, such as the eye marker devices described in U.S. patent application Ser. No. 13/427,253, which is fully incorporated herein by reference. Other embodiments may be configured for use with other eye marker devices.

Figure 2:
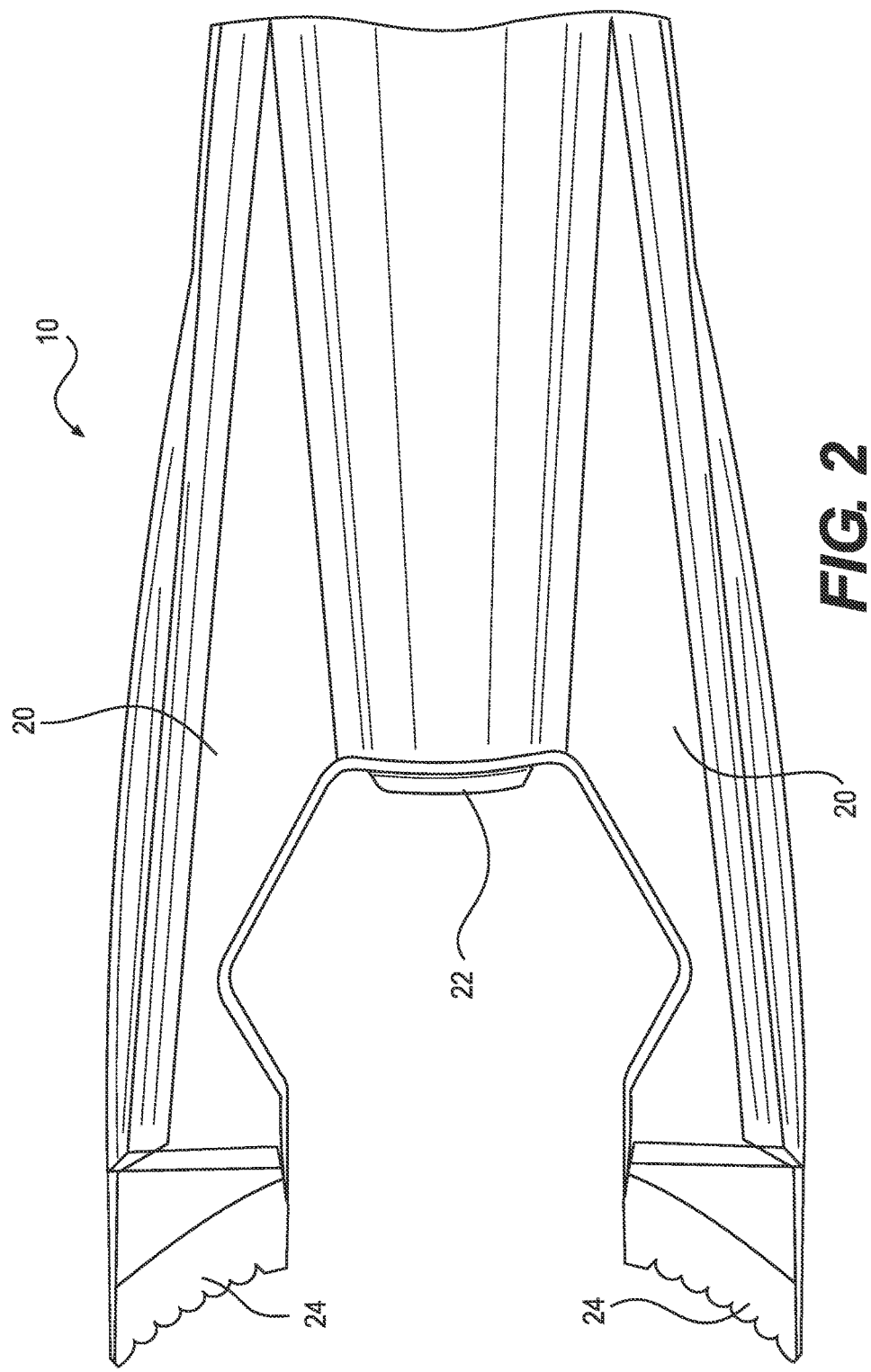
FIG. 2 is a perspective view of an embodiment of an eye marker tip.
Figure 3:
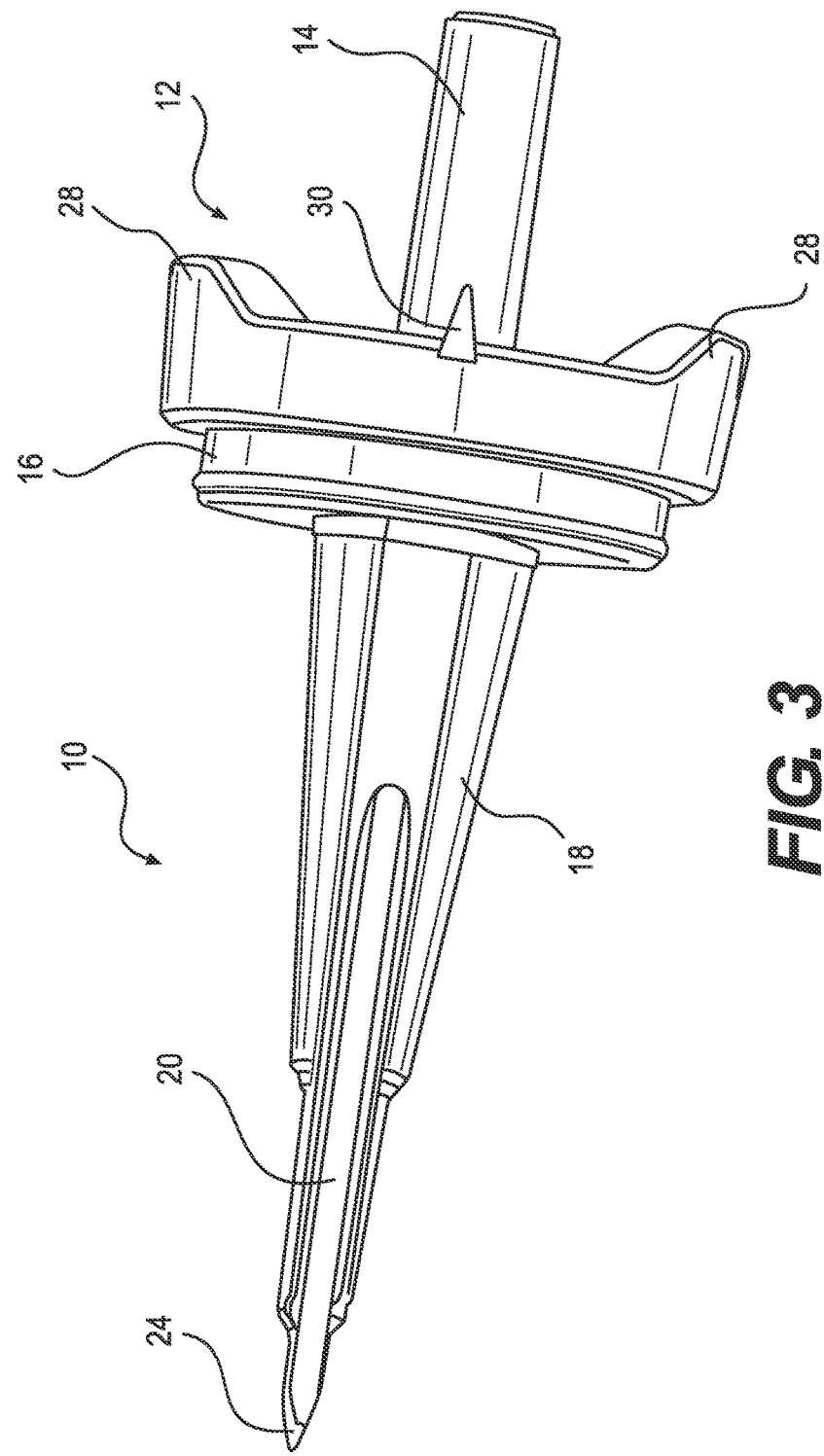
FIG. 3 is another perspective view of an embodiment of an eye marker tip.
Figure 4:
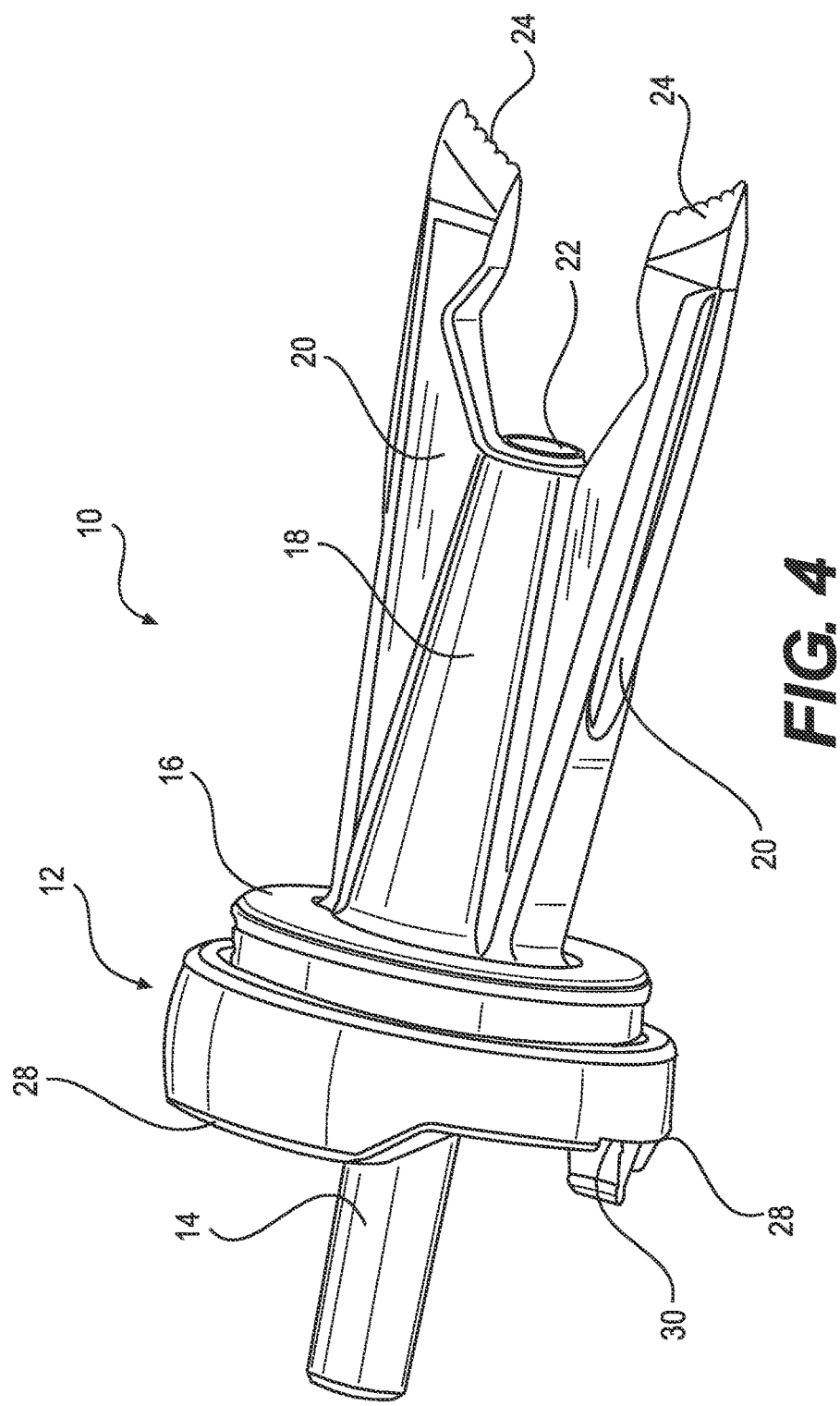
FIG. 4 is another perspective view of an embodiment of an eye marker tip.
Figure 5:
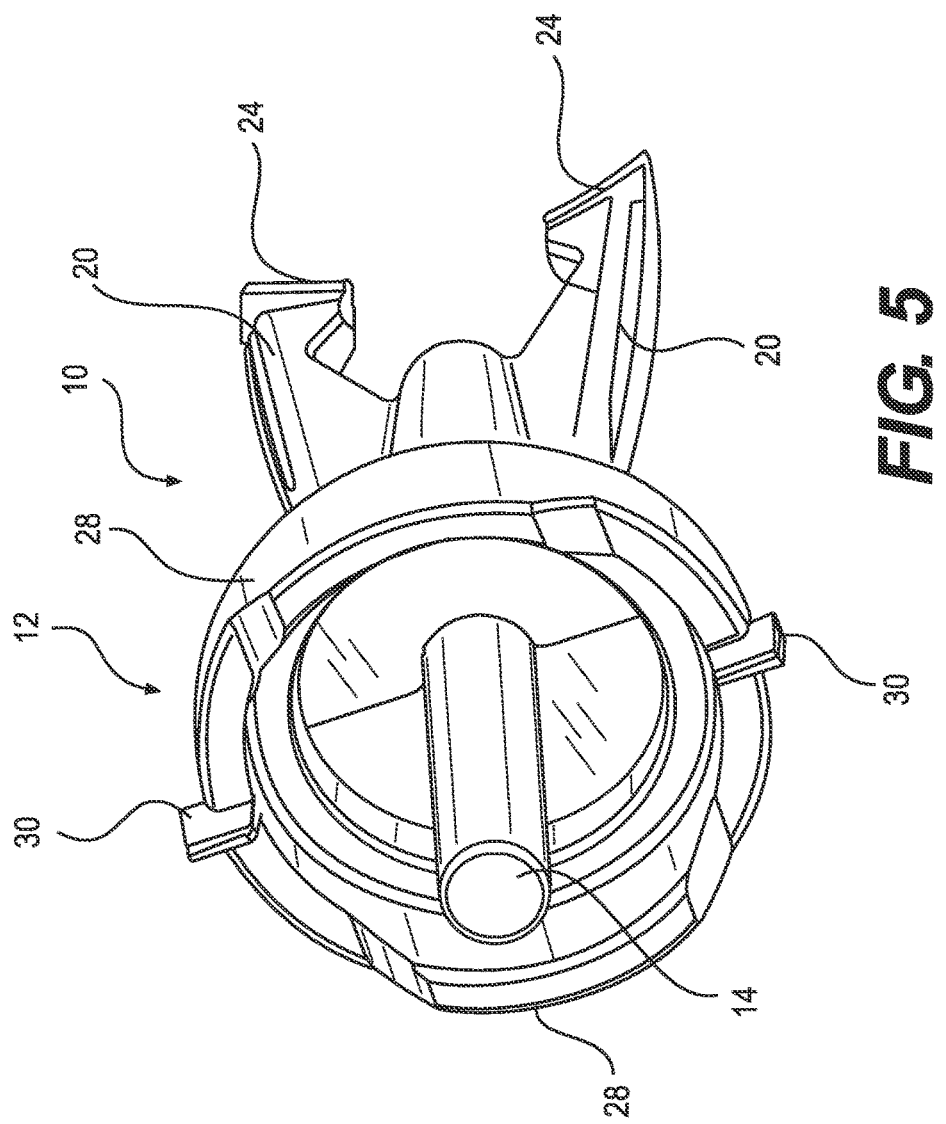
FIG. 5 is a bottom perspective view of an embodiment of an eye marker tip.

Eye marker tips as described herein have a proximal end for connection or removable attachment to an eye marker device, and a distal end having one or more marking elements. For example, eye marker tip 10 comprises a distal end, at the left side of FIG. 1, and a proximal end, at the right side of FIG. 1. The distal end in this embodiment comprises a base 12 with a post 14 extending from the base 12. In this embodiment, base 12 and post 14 are generally cylindrical or ovular, although other embodiments that include a post may use alternate shapes for post 14. Base 12 and post 14 may include structure for aligning the eye marker tip 10 with a corresponding eye marker device in a removably attached configuration, such as the protrusions 28 that project proximally from base 12 in the embodiment shown in FIGS. 1-6. Other embodiments may feature one or more such protrusions or similar structure, or indentations or grooves that correspond to protrusions in a corresponding eye marker device, on the eye marker tip. Some embodiments may include an indicator arrow (or other shape), such as an arrow, on the surface of the lower portion, to indicate the position of the eye marker tip relative to the corresponding eye marker device when attached. Embodiments of the eye marker tip 10 may have a longitudinal axis from the distal end to the proximal end, and base 12 and post 14 may be centered or aligned with the longitudinal axis as shown in FIGS. 1 and 3, for example. In this embodiment, the post 14 has a first end and a second end, whereby the post 14 extends proximally from the proximal end of the base 12, such that base 12 and post 14 are aligned with the longitudinal axis.

Some embodiments of eye marker tip 10 include a post 14 configured to allow light to pass between the first end and the second end. The light may originate from the proximal end, provided by a light source, such as an eye marker device, and may be transmitted distally. For example, in some embodiments, the post 14 features a hollow shaft running through the long axis between the first and second ends, along the longitudinal axis of the eye marker tip 10. Other embodiments may feature a shaft with a hollow interior portion. As further examples, post 14 in some embodiments may be made from a transparent or translucent material, or post 14 may include a portion that is made from a transparent or translucent material. In embodiments having a post 14 with a hollow shaft, hollow interior portion, transparent or translucent material, or combinations thereof, light may pass through post 14 and other components of the eye marker tip 10 described below. Embodiments with a post 14 configured to allow light to pass between the first end and the second end may provide additional features as described below.

Embodiments of the eye marker tip 10 may include one or more position indicators 30. A position indicator 30 may be located in a region that is visible to the user. For example, a position indicator 30 may be disposed on the external surface of the base 12. In some embodiments, a position indicator may be placed on an interior surface of the base 12, provided that the indicator is visible to the user. In embodiments with a position indicator placed on an interior surface of base 12, the position indicator may be a groove that is pigmented. In some embodiments, the position indicator may include a surface marking, such as arrow or notch, that provides a visual representation of the position of the eye marker tip 10 relative to an eye marking device (not shown in the drawings). Other embodiments may include one or more types of position indicators.

The eye marker tip 10 may include structural elements for removably attaching the eye marker tip 10 to an eye marking device (not shown in the drawings). The attachment elements used in an embodiment will depend on the corresponding eye marker device. For example, the base 12 in the eye marker tip 10 of FIGS. 1-6 includes protrusions 28 that project proximally from base 12 for positioning the eye marker tip on a corresponding eye marking device (not shown in the drawings).

Embodiments of the eye marker tip 10 may include structure protruding distally from the distal side of the base 12, including, for example, an upper area, a light channel, and one or more marking wings. In the embodiment shown in FIGS. 1-6, an upper area 16 extends distally from base 12, is generally cylindrical or ovular, and has a diameter slightly less than the diameter of the base 12. In this embodiment, light channel 18 and a pair of marking wings 20 protrude distally from the upper area 16. In some embodiments, structure such as a light channel or a marking wing may protrude from base 12, or from both base 12 and upper area 16. In some embodiments, light channel 18 may protrude radially and distally from one or more of base 12, upper area 16, and light channel 18. In the embodiment shown in FIGS. 1-6, marking wings 20 extend distally from upper area 16 and radially and distally from opposite sides of light channel 18. It should be appreciated that a number of configurations are possible without departing from the principles described herein.

Light channel 18 may be configured to allow light to pass from the eye marker device (not shown), through post 14, and through the light channel 18. For example, light channel 18 may be hollow, include a hollow shaft or a hollow interior portion, be made of a transparent or translucent material, include a transparent or translucent region. In embodiments with a light channel 18 configured to allow light to pass, the light may be visible to the patient through an opening 22 at a distal end of the light channel 18. In some embodiments, opening 22 may be physically open to allow light to pass. In other embodiments, opening 22 may include a transparent or translucent material or region to allow light to pass. As illustrated in FIG. 6, the opening 22 in some embodiments may include a lens 26 that allows the light to appear to the user in a particular shape, such as a circle, to assist the user in maintaining a point of focus.

As discussed above, embodiments of the eye marker tip 10 include one or more marking wings 20. A marking wing 20 extends distally from one or more other components of the eye marker tip 10, such as base 12, upper portion 16, and light channel 18. In the embodiment shown in FIGS. 1-6, marking wings 20 extend from the base 12 towards the distal end of the light channel 18. In this embodiment, the distal end of the marking wings 20 extends distally farther than the opening 22 and the distal end of the light channel 18. In this embodiment, the marking wings 20 extend radially outwardly from the light channel 18, but other geometries are possible for other embodiments. A marking element 24 is contained on the top portion of each marking wing 20. It should be appreciated that other configurations and relative positions are possible, provided that a marking element 24 extends distally past the distal-most end of another component. Otherwise, the distal-most end of another component may prevent a marking element 24 from contacting an ocular surface and applying a mark.

The marking element 24 may be positioned on the distal end of a marking wing 20. Generally, a marking element 24 may be an element configured to apply or place a mark, such as an ink mark, or another indicator, on the surface of the cornea, sclera, or the sclera/cornea junction (collectively referred to as the eye surface). The marking element 24 may comprise a material suitable for retaining and/or delivering the ink (or other indicator). For example, materials such as plastic, paper, metal, gelatin, hydrogel, aerogel, solid and gelled sugar/carbohydrate may be used. FIG. 2 shows an embodiment of a marking element 24 in more detail. The marking element 24 may comprise a plurality of edges disposed on the end of a marking wing 20.

An eye marker tip 10 may include one or more mechanisms for storing ink (or another indicator), transferring ink to a marking element 24, and/or transferring ink from a marking element 24 to the eye surface. For example, the marking element 24 may be pre-inked, whereby a tip or other portion of marking element 24 is infused with ink prior to packaging or shipment to the user, for example. In some pre-inked embodiments, a user may not need to reapply ink to the marking element 24. Additionally, the marking element 24 may be used repetitively, if necessary, on the same patient for providing more than one mark without having to constantly reapply ink to the marking element 24. For example, the volume of pre-inked ink may be sufficient for more than one application of marks. An eye marker tip 10 may use an indicator other than ink. For example, in some embodiments, the marking element 24 may apply a tack or other like indicator on the surface of the cornea, sclera, or the sclera/cornea junction. In some embodiments, marking element 24 may apply a cut to the top surface of the cornea, the epithelium, and not through Bowman's membrane. The cut may be the indicator, or may be used in combination with another indicator. In some embodiments, the cut could be seen using a special microscope lighting, or alternatively an ink indicator could be placed on the cornea during the procedure to identify the cut or disruption of the epithelium.

The marking element 24 may also contain a material and/or structure that provide a formed indicator reservoir or a channel for the ink (or other indicator). The reservoir or channel may permit a passive flow of ink to the marking element 24 surface. The marking element 24 may include, for example, a material with nanotubules and/or nanochannels or the like. The marking element 24 may include a material containing pigment/indicator encapsulated microbeads and/or microgranules, that are able to release the indicator using a release mechanism. The release mechanism may be, for example, making contact with pressure, water, the tear film, heat, a combination of one or more such mechanisms, or another release mechanism as may be known in the art. Further, the marking element 24 may contain a microprint cartridge mechanism, in which an indicator is jetted from the marking element 24 in a desired pattern by an electronic or non-electronic mechanism. The marking element 24 may contain, or be in fluid communication with, a compressible reservoir of indicator/ink such that compression forces the indicator/ink to the surface of the marking element 24. The marking element 24 may be coated with a biocompatible glue or gel that is covered with the indicator/ink, such that the glue or gel acts as an adhesive to keep the indicator/ink attached to the marking element 24 and such that the indicator/ink constitutes the external surface of the marking tip/glue/gel complex, or the marking element 24 may be a biocompatible glue or gel that is mixed with the indicator such that the composite of the glue/gel/indicator/ink constitutes the external surface of the nib. Embodiments of the marking element 24 may include combinations of mechanisms. Embodiments of the eye marker tip 10 may include marking elements 24 that have similar or different mechanisms or combinations of mechanisms. A mechanism may be included in one or more components of the eye marker tip 10, such as a marking wing 20 and light channel 18. For example, light channel 18 may include a reservoir in fluid communication with channels along a marking wing 20 leading to marking element 24. Other configurations for including one or more mechanisms are possible without departing from the principles of this disclosure.

The eye marker tip 10 may be formed from a clear, transparent, or translucent plastic, metal, paper, biopolymer, or the like, or a combination of plastic and metal, or the like. In some embodiments, components of the eye marker tip 10 may be formed of one or more different materials. In some embodiments, portions of components of the eye marker tip 10 may be formed of one or more different materials, or feature portions that are transparent or translucent. The plastic may allow light to pass through all or a portion of the eye marker tip to illuminate a surface, such as the surface of a patient's eye.

Figure 7A:
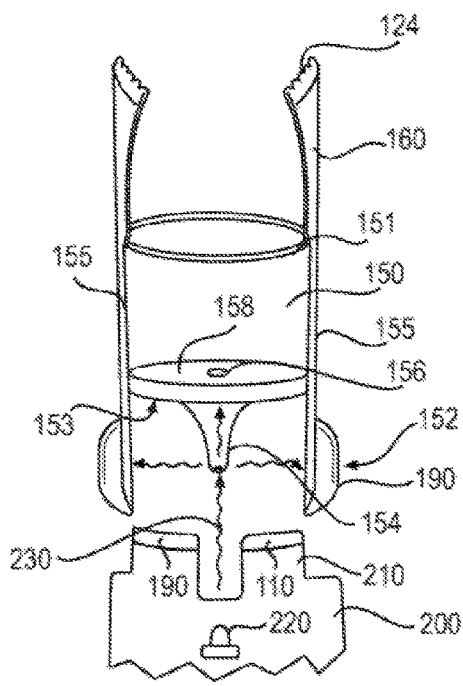
FIGS. 7A, 7B, and 7C are side, top, and bottom views, respectively, of another embodiment of an eye marker tip.
Figure 7B:
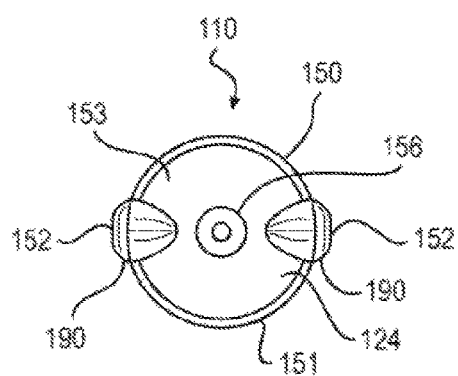
Figure 7C:
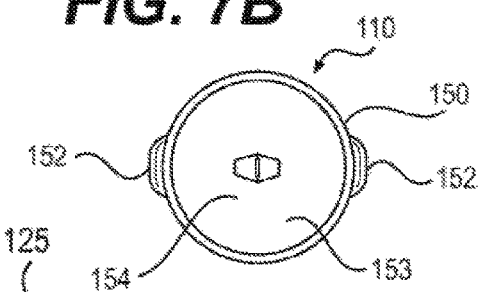

FIGS. 7A, 7B, and 7C are side, top, and bottom views, respectively, of another embodiment of an eye marker tip 110. In this embodiment, eye marker tip 110 includes marking elements 124, housing 150, cylindrical ring 151, base 153, axial dial magnifying lens 152, parabolic (or prismatic) light deflector 154, and fixation button 156. In some embodiments, housing 150 may be a completely or partially enclosed cylinder, with marking elements 124 extending therefrom through marking wings as described above. In the embodiment shown in FIGS. 7A-7C, housing 150 is a hollow or an open structure, in which side walls 155 and base 153 form an H-shaped profile when viewed from a side. Embodiments may include one or more side walls 155, and side walls may be distributed radially around base 153 in a number of possible configurations. The embodiment shown in FIGS. 7A-7C includes two side walls 155 disposed on opposite sides of base 153. Further, in this embodiment, marking wings 160 extend proximally from side walls 155. Other embodiments may include side walls 155 that do not have marking wings, and marking wings that do not extend from a side wall 155.

In the embodiment illustrated in FIGS. 7A-7C the eye marker tip 110 contains a bottom portion (toward the bottom of FIG. 7A) and a top portion (toward the top of FIG. 7A). The bottom portion may be configured for attachment to an eye marker device 200, such as the eye marker devices described in U.S. patent application Ser. No. 13/427,253, which is fully incorporated herein by reference. In embodiments of an eye marker device 200 with a ring dial 210, the bottom portion of the housing 150 may be configured to be placed over the ring dial 210. In the embodiment shown in FIGS. 7A-7C the bottom portion of the housing 150 has a diameter slightly larger than the diameter of the device 200 or ring dial 210, that the hollow housing 150 may engaged in a removably attached or mated configuration. Other embodiments may use an alternative mechanism to attach an eye marker tip 110 to an eye marker device 200.

Embodiments of an eye marker tip may include a magnifier lens to assist users in reading the settings on a ring dial or eye marker device. A lens may be included in a base, sidewall, or other structure, as appropriate for use with a corresponding ring dial or eye marker device. For example, FIGS. 7A-7C shows a pair of magnifier lens 152 on eye marker tip 110. In the embodiment shown in FIGS. 7A-7C, magnifier lens 152 is disposed within the housing 150, and on a distal portion of side walls 155, in close proximity to the bottom portion, or use with ring dial 210. Attaching eye marker tip 110 to eye marker device 200 aligns lens 152 to magnify a portion of ring dial 210, indicating the relative position of the eye marker tip 110. Other embodiments may position the magnifier lens as needed for use with a corresponding ring dial. In the embodiment shown in FIGS. 7A-7C, the magnifier lens 152 generally spans the width of the interior of the housing 150, but other embodiments may use a larger or smaller lens relative to the housing 150 or side wall 155. In some embodiments, not all side walls 155 include a lens.

Embodiments of an eye marker tip may incorporate a parabolic or prismatic light deflector to receive light from an eye marker device, and deflect the light. The light deflector may allow a portion of light to pass distally, as described above with respect to the FIGS. 1-6. For example, the eye marker tip 110 in FIGS. 7A-7C includes a light deflector 154 disposed centrally on the base 153, generally between a pair of magnifier lens 152. The light deflector 154 is designed to deflect light from a light source, such as LED 220 in an eye marker device 200, towards the outer axially outer edges of the base 153, and towards the inner side surfaces of the housing 150 and side walls 155, thereby forming a deflected light shape. In this embodiment, the light deflector 154 is disposed above the eye marker device 200, such that the light projected from LED 220 through the eye marker device 200 hits the light deflector 154, and is deflected axially as shown in FIG. 7A. Some embodiments of the eye marker device 200 may include an opening 230 in the center of the ring dial 210. In some embodiments, the light deflector 154 may be configured to align with an opening 230 for receiving light. Base 153 may further include a magnification lens 158 for focusing light received from an eye marker device. For instance, a base 153 may magnify light deflected axially, and/or may focus light allowed to continue distally. The magnification lens may form a magnified light shape. In some embodiments, base 153 comprises a magnification lens 158.

When light contacts the light deflector 154, a portion of the light may proceed distally through the center of the magnifier lens 158. This creates a visible light dot for viewing by the patient. The light deflector 154 in the embodiment shown in FIGS. 7A-7C is generally disposed on the underside of the base 153, and in some embodiments the magnifier lens 158 which may face the device and ring dial. In such embodiments, a fixation button 156 may be positioned on the proximal side of base 154 and/or the magnifier lens 158. The light protrudes distally through the fixation button 156, or in close axial proximity to the fixation button 156, to create a light dot (or other shape) for viewing by the patient.

Figure 8B:
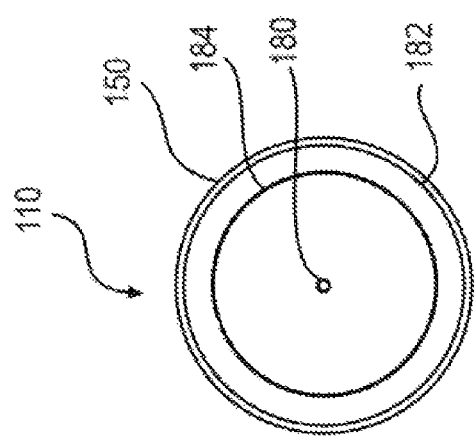
FIGS. 8A and 8B illustrate an alignment technique that may be incorporated into embodiments of an eye marker tip.
Figure 8A:
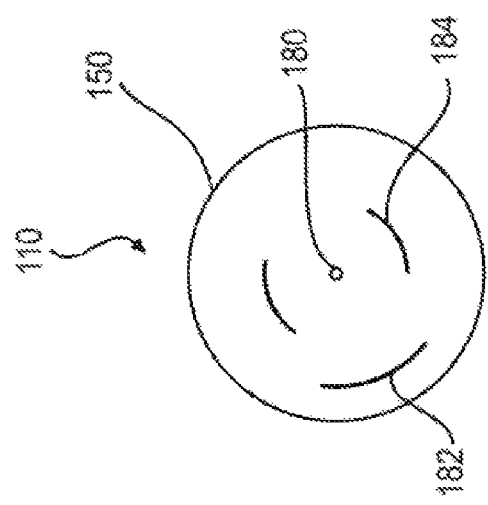

In embodiments with a light deflector 154, a portion of the light deflected axially by the parabolic or prismatic light deflector 154 proceeds towards the outer axial edges of the base 154 and/or magnifier lens 158, and towards the inner axial side surfaces of the housing 150 and side walls 155. The deflected light creates one or more visible circles of light when viewed from the proximal direction (top of FIG. 7A, viewing toward the bottom of FIG. 7A) by the patient. When the eye marker tip 110 is correctly aligned with respect to the patient's eye, the patient should perceive both the central light dot (or other shape) emitted from the fixation button 156, and at least one outer circle of light along the outer edges of the base 153 and/or magnifier lens 158. When the patient's eye is in perfect alignment with the eye marker tip 110, the central light dot 180 should be perfectly concentric with the outer circle of light 182, as shown in FIG. 8A. The light circle 184 along the edge of base 153 may also be visible, and at perfect alignment should be concentric with the central light dot 180 and outer circle of light 182, and outer circle of light 182 may also appear to form a complete circle. More than one circles of light may appear, and in some embodiments the distance between the light source and the patient's eye may determine the number of visible light circles. In some embodiments, the length of the eye marker tip from the distal end to the proximal end, may determine the number of visible circles. In some embodiments with an enclosed and/or cylindrical housing, the length of the enclosed cylindrical portion may determine the number of visible circles. When the patient's eye and eye marker tip 110 are incorrectly aligned, the patient may view the light dot 180, but the outer circle of light 182 and/or light circle 184 may appear discontinuous, out of alignment, and/or not visible at all, as shown in FIG. 8B.

The alignment technique described above has application beyond the eye marker tip and eye marker device described in this application and U.S. patent application Ser. No. 13/427,253. For instance, the alignment technique may be employed in various ophthalmic diagnostic devices in which alignment of the eye relative to a device is useful or necessary to produce accurate results.

In some embodiments, the eye marker tip 110 may contain an axis dial 190. In the embodiment shown in FIGS. 7A-7C, the axis dial 190 comprises one or more protrusions extending axially from the bottom portion of the eye marker tip 110, projecting from the housing 150 and externally surface of side walls 155. Other embodiments may feature one or more protrusions, in locations and configurations other than the demonstrative configuration shown in FIGS. 7A-7C. The axis dial 190 may be rotationally engaged to the housing 150 for allowing the axis dial 190 to rotate around the housing 150 for adjusting the magnifier lens 158.

Figure 7D:
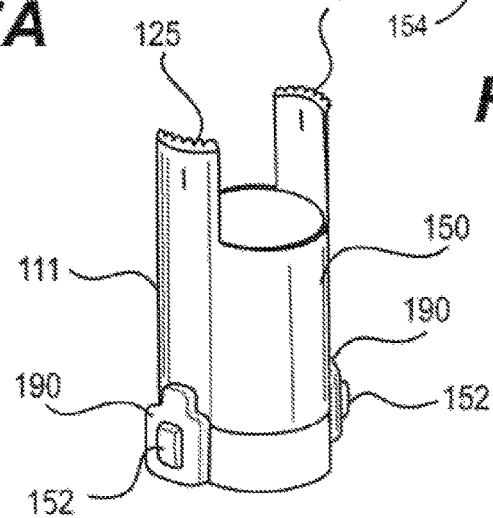
FIG. 7D shows a perspective view of another embodiments of an eye marker tip.

The eye marker tip 110 may contain an elongate extension such as marking wings 160 that contains the marking element 124. The marking element 124 may contain the structures and operate as described above. Some embodiments may be enclosed, such that the magnifier lens 158 and fixation button 156 are visible only from looking at a top view of the eye marker tip. For instance, eye marker tip 111 shown in FIG. 7D includes an enclosed housing, such that the single sidewall forms a continuous cylinder. In embodiments incorporating an alignment technique, the length of the housing may determine the number of visible light circles produced, as discussed above. Eye marker tip 111 also includes LRI marking tips 125, whereas the embodiment shown in FIG. 7A includes toric marking tips 124. It should be understood that an embodiment of an eye marker tip may feature a marking tip appropriate for the type of marking necessary. Some embodiments may feature removable marking tips, such that a user may replace, for instance, a toric marking tip 124 with an LRI marking tip 125.

In some embodiments, all or a portion of the eye marker tip may be disposable. For example, the upper portion of an eye marker tip that contains the marking element may be removable from the lower portion and disposable. Such embodiments allow a portion of the eye marker tip to be disposed and a new portion containing the marking element to be engaged to the lower portion of the eye marker tip. Such embodiments allow for quickly replenishing ink or indicator, and for rapid and sanitary applications of marks on a patient's eye. The disposable upper portion and the remaining lower portion may be engaged by a number of selectively securing ways. For example, and not meant to be limiting, the disposable portion may contain a male section, and the remaining portion may have a female portion that are selectively secured to one another, or vice-versa. Alternatively, the one portion may have a rib that slides within a channel on the other portion. The disposable portion and the remaining portion may be constructed of similar or dissimilar materials. For example and not meant to be limiting, the disposable portion may be constructed of plastic and the remaining portion of the eye marker tip may be constructed of metal.

An eye marker tip may include a stress-breaking feature to prohibit re-use of the eye marker tip, which may be useful in numerous instances, such as embodiments in which the ink supply mechanism is not intended to be refillable, and in embodiments in which the entire eye marker tip is disposable. Disposing of an eye marker tip after a single use also ensures that users maintain high levels of sanitation. A stress-breaker feature causes a mechanical failure in the eye marker tip after a certain action, e.g., the eye marker tip breaks when a user attempts to remove the tip from the eye marker device.

FIGS. 9A and 9B show an exemplar embodiment of an eye marker tip 310 having a stress-breaker feature. Eye marker tip 310 includes marking tip 324 projecting distally from marking wing 320. The housing 350 connects marking wings 320 and base 316. The housing 350 may also include axis dial protrusions 190 and magnifier lens 352, as described above. Magnifier lens 352 may include an axis alignment line 353, to assist a user with precise alignment of the eye marker tip 310 on a corresponding eye marker device. An interior surface of the housing may include an axis alignment line 354, such as would be visible from the exterior, for the same purpose. Base 316 may include a fixation button 356, and may comprise a magnifier lens as described above. Although FIG. 9A does not show a mechanism for light from a corresponding eye marker device 400 to deflect and/or pass through base 316, embodiments may include such features as described above. As shown in FIG. 9B, this embodiment does not feature a circular housing 350 or a circular base 316. Thus, embodiments incorporating an alignment technique as described above may require a patient to align an incomplete outer circle or arc length with a central light dot, and may also include an interior circle of light formed by a magnifier lens incorporated on base 316. Some embodiments may include a segmented cylinder housing that incorporates the alignment technique and also includes a region for a stress-breaker feature.

The stress-breaker feature in FIG. 9A is built into base 316. Base 316 connects to housing 350 at break-away zones 360. Break-away zones 360 may comprise reduced surface area or volume, and may also include materials that suffer brittle or mechanical failure upon application of a threshold force. In this embodiment, the eye marker tip 310 is configured to snap onto a corresponding eye marker device 400, such that groove lock projections 380 mate with indentations 381 on eye marker device 400. Indentations 381 may be circular, such that eye marker tip 310 may be rotated for adjustment to the desired location. Other embodiments may incorporate a different mechanism for connecting an eye marker tip to a corresponding eye marker device, such as including an annular groove lock projection on an eye marker device, and including a corresponding indentation on the eye marker tip.

In the embodiment shown in FIGS. 9A and 9B, eye marker tip 310 is configured to withstand the force of attaching eye marker tip 310 to eye marker device 400. For example, break-away zones 360 do not fail when a user attaches the eye marker tip 310 to the eye marker device 400. As a further example, break-away zones 360 do not break when groove lock projections 380 slightly expand to fit around the upper dial portion of eye marker device 400, or when groove lock projections 380 snap into the indentations 381. However, when a user attempts to detach eye marker tip 310 from eye marker device 400, the user must apply a bending force to the housing to expand the distance between groove lock projections 380 a sufficient distance to fit over the upper portion of the eye marker device 400. The bending force causes a failure or break at one or more break-away zones 360, rendering the eye marker tip 310 unsuitable for further use. As a consequence, a user must use a new eye marker tip 310 (preferably sterile and/or sanitized) for the next patient.

Figure 10:
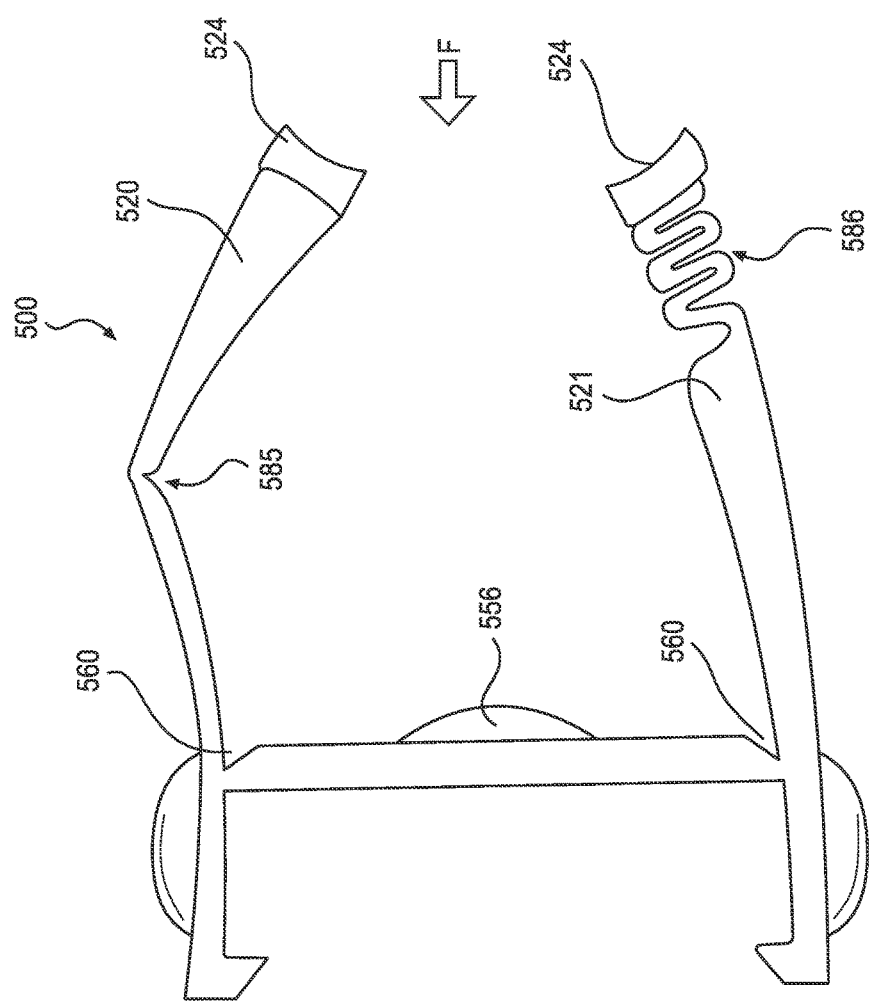
FIG. 10 shows an embodiment of an eye marker tip having flexion points or regions.

Some embodiments of an eye marker tip may include a marking wing or housing having one or more flexion points or regions. A flexion point or region allows the marking element to recoil or bend on the application of a force from the proximal direction, on the marking elements. The recoil or bend may be used to assist the user with aligning more than one marking elements, ensure contact between marking elements and the patient's eye, and as a mechanism for delivering ink or another indicator from the housing or marking wing to a marking element. FIG. 10 shows two embodiments of a marking wing having a flexion point or region. In this embodiment, eye marker tip 500 includes a first marking wing 520 having a single flexion point 585. Other embodiments may include more than one flexion point, and at various locations on a marking wing or housing. When force F acts on marking element 524, marking wing 520 may bend at flexion point by a desired amount, thereby allowing a desired displacement change of the marking element 524 relative to the eye marker tip 500, other marking elements, and/or the patient's eye. An eye marker tip may include more than one type of flexion feature. For example, eye marker tip 500 includes a second marking wing 521, having a flexion region 586 with multiple bends. Flexion region 586 may allow displacement of marking element 524 upon application of force F. the displacement of a marking element may be useful for aligning multiple marking elements, ensuring one or more marking elements contact the patient's eye at the same time and/or with the desired force. It should be appreciated that flexion points and regions may be incorporated into an eye marker tip in more than one location and configuration, and provide one or more advantageous benefits.

The terminology used herein is for the purpose of describing particular embodiments only and is not intended to be limiting of the approach. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The apparatus and methods described herein may be embodied in other specific forms without departing from the principles described above. The present embodiments are therefore to be considered in all respects as illustrative and not restrictive, the scope of this application being indicated by the claims of the application rather than by the foregoing description, and all changes which come within the meaning and range of equivalency of the claims are therefore intended to be embraced therein.

That which is claimed:

1. An eye marker tip for removable attachment to an eye marker device comprising:
    a base, including protrusions projecting proximally from the base for positioning the eye marker tip on the eye marker device and a position indicator disposed on an external surface of the base and visible to a user;
    a post extending proximally from a proximal end of the base such that the base and the post are aligned with a longitudinal axis, the post having a hollow shaft, hollow interior portion, transparent material or translucent material or combination thereof to permit light passage;
    a light channel to allow light from a light source to pass from the eye marker device through the post and visible to a patient through an opening at a distal end of the light channel; and
    a marking tip extending fixed to the base and extending distally therefrom towards the distal end of the light channel, the marking tip comprising at least one marking wing extending radially outwardly from the light channel and extending distally further from the opening at the distal end of the light channel and a marking element positioned at a distal end of the at least one marking wing and configured to transfer an indicator onto an eye surface.

2. The eye marker tip of claim 1, further comprising an annular ring having an internal side and external side extending from an outer edge of the base and forming a cavity within the internal side of the annular ring and bottom portion of the base.

3. The eye marker tip of claim 1, wherein the at least one marking wing includes a second marking wing, wherein the marking wings are positioned on opposed sides of a middle portion of the base and extend outward from the middle portion.

4. The eye marker tip of claim 1, wherein the at least one marking wing includes two marking wings in spaced-apart relationship extend upward from a first side of the base and a hollow middle portion spans between the two marking wings.

5. The eye marker tip of claim 1, wherein the marking element is pre-inked.

* * * * *